United States Patent
Leigh

(10) Patent No.: US 10,940,320 B2
(45) Date of Patent: Mar. 9, 2021

(54) DISTRIBUTED IMPLANTABLE HEARING SYSTEMS

(71) Applicant: Cochlear Limited, Macquarie University (AU)

(72) Inventor: Charles Roger Aaron Leigh, North Epping (AU)

(73) Assignee: COCHLEAR LIMITED, Macquarie University (AU)

(*) Notice: Subject to any disclaimer, the term of this patent is extended or adjusted under 35 U.S.C. 154(b) by 153 days.

(21) Appl. No.: 15/700,370

(22) Filed: Sep. 11, 2017

(65) Prior Publication Data
US 2018/0028825 A1    Feb. 1, 2018

Related U.S. Application Data

(63) Continuation of application No. 14/293,121, filed on Jun. 2, 2014, now abandoned.

(51) Int. Cl.
| A61N 1/36 | (2006.01) |
| A61N 1/372 | (2006.01) |
| H04R 25/00 | (2006.01) |

(52) U.S. Cl.
CPC ..... *A61N 1/37229* (2013.01); *A61N 1/36038* (2017.08); *H04R 25/606* (2013.01); *H04R 25/554* (2013.01)

(58) Field of Classification Search
CPC .......................... A61N 1/36036; A61N 1/0541
See application file for complete search history.

(56) References Cited

U.S. PATENT DOCUMENTS

| 3,764,748 | A | * | 10/1973 | Branch | H04R 25/606 |
| | | | | | 607/57 |
| 4,696,287 | A | | 9/1987 | Hortmann et al. | |
| 5,913,815 | A | * | 6/1999 | Ball | H04R 25/606 |
| | | | | | 600/25 |
| 5,991,664 | A | | 11/1999 | Seligman | |
| 6,137,889 | A | | 10/2000 | Shennib et al. | |
| 6,859,666 | B1 | | 2/2005 | Clark et al. | |
| 7,120,501 | B2 | | 10/2006 | Boylston et al. | |
| 2002/0099421 | A1 | | 7/2002 | Goldsmith et al. | |
| 2004/0093040 | A1 | | 5/2004 | Boylston et al. | |
| 2005/0033384 | A1 | | 2/2005 | Sacha | |
| 2006/0107744 | A1 | * | 5/2006 | Li | G01H 9/006 |
| | | | | | 73/657 |
| 2007/0135884 | A1 | | 6/2007 | Risi | |
| 2007/0183613 | A1 | * | 8/2007 | Juneau | A61F 11/10 |
| | | | | | 381/322 |
| 2009/0216296 | A1 | * | 8/2009 | Meskens | A61N 1/36036 |
| | | | | | 607/57 |
| 2011/0130622 | A1 | | 6/2011 | Ilberg | |
| 2011/0144749 | A1 | * | 6/2011 | Kim I | A61N 1/36036 |
| | | | | | 623/10 |

FOREIGN PATENT DOCUMENTS

EP        0259906 A2    3/1988

* cited by examiner

*Primary Examiner* — Michael J D Abreu
(74) *Attorney, Agent, or Firm* — Edell, Shapiro & Finnan, LLC

(57) ABSTRACT

Presented herein are distributed implantable hearing systems that have at least a main implant module that is physically separated from a distally positioned inner radio-frequency (RF) coil. Embodiments presented herein may include a main implant module positioned within a recipient's mastoid and an implantable coil positioned within a recipient's middle ear cavity.

23 Claims, 11 Drawing Sheets

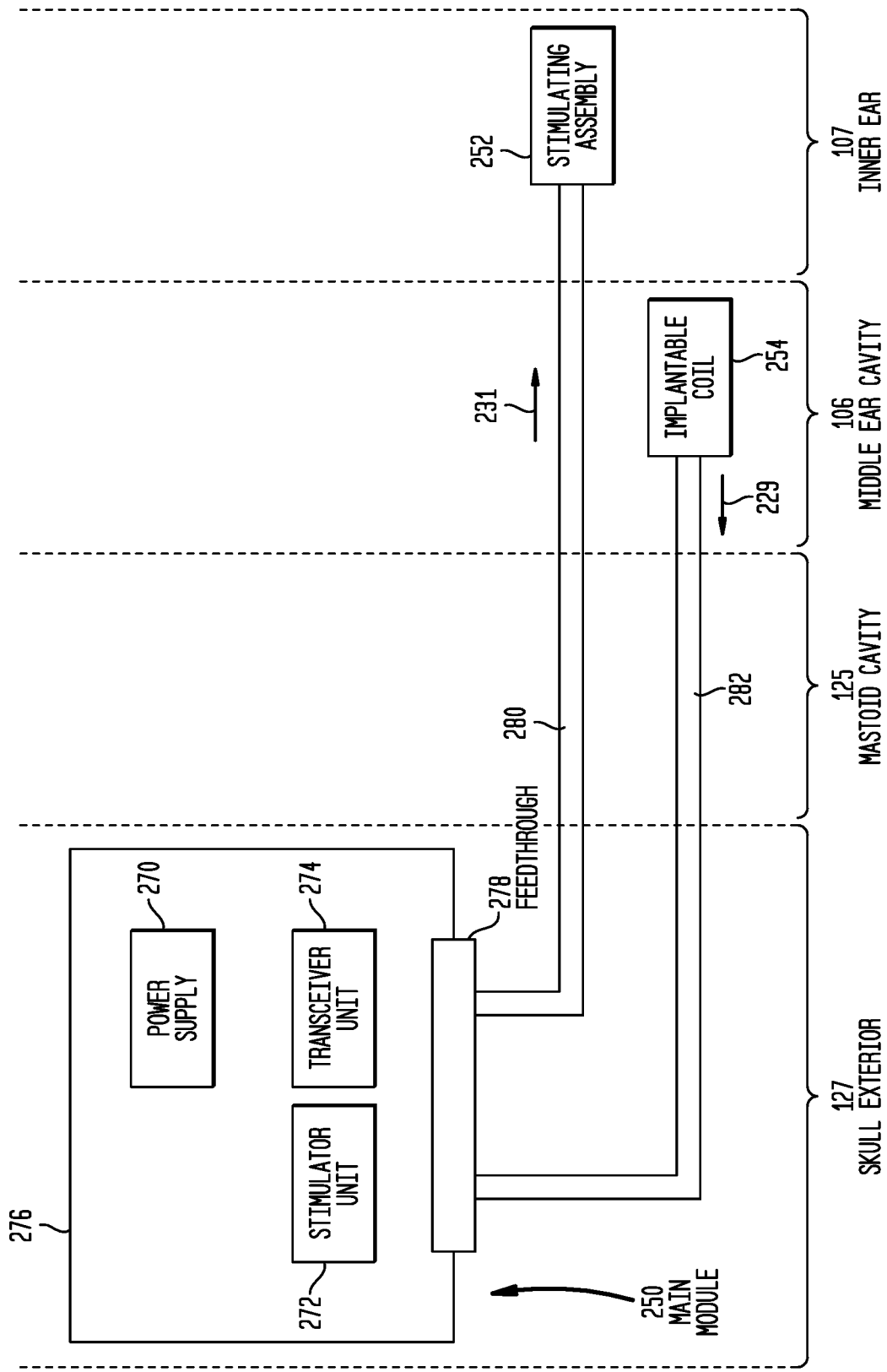

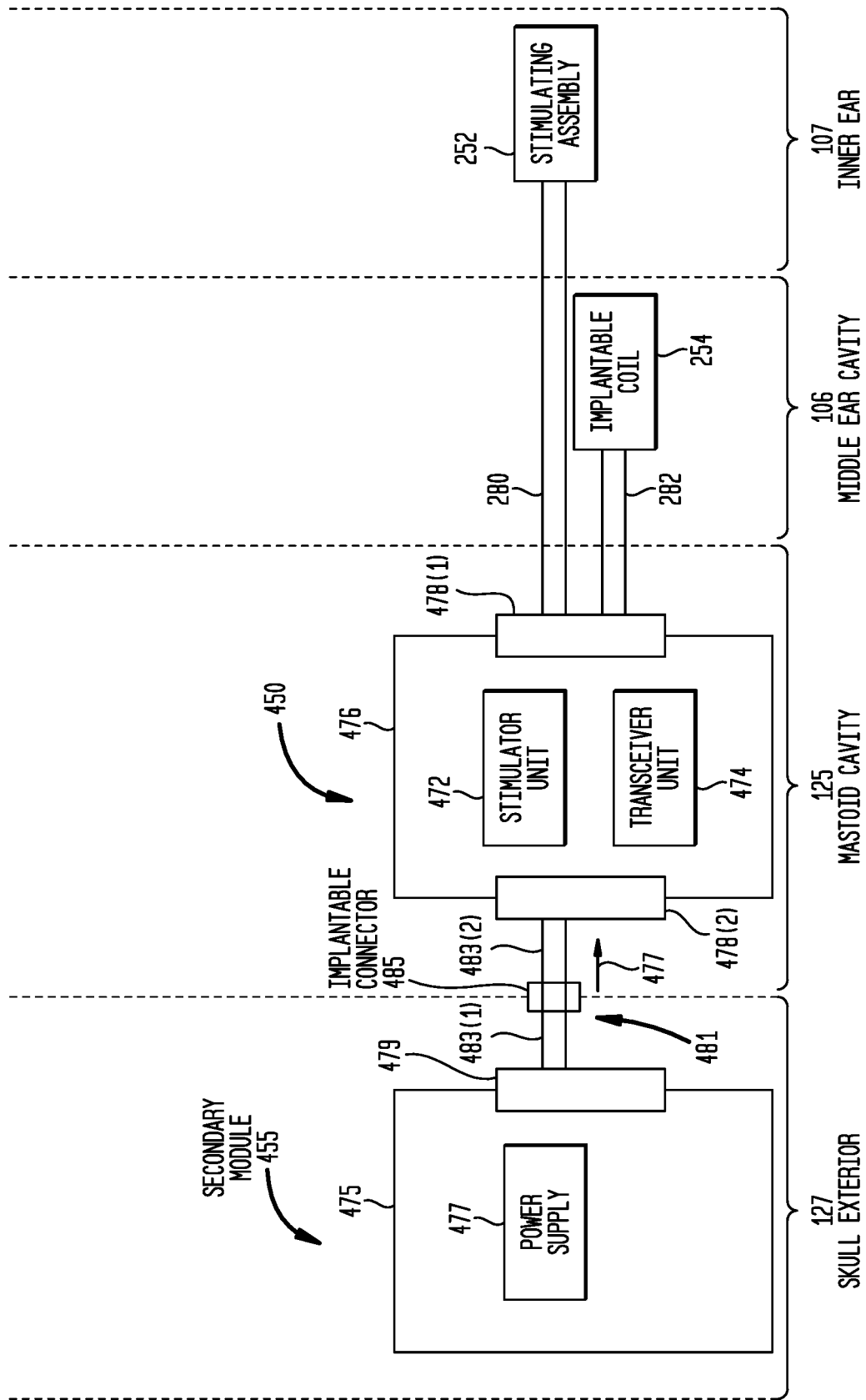

DISTRIBUTED IMPLANTABLE HEARING SYSTEMS

CROSS-REFERENCE TO RELATED APPLICATION

This application is a continuation of U.S. patent application Ser. No. 14/293,121, filed Jun. 2, 2014, the entire contents of which is incorporated herein by reference.

BACKGROUND

Field of the Invention

The present invention relates generally to implantable hearing systems, and more particularly, to distributed implantable hearing systems.

Related Art

Hearing loss, which may be due to many different causes, is generally of two types, conductive and/or sensorineural. Conductive hearing loss occurs when the normal mechanical pathways of the outer and/or middle ear are impeded, for example, by damage to the ossicular chain or ear canal. Sensorineural hearing loss occurs when there is damage to the inner ear, or to the nerve pathways from the inner ear to the brain.

Individuals who suffer from conductive hearing loss typically have some form of residual hearing because the hair cells in the cochlea are undamaged. As such, individuals suffering from conductive hearing loss typically receive an auditory prosthesis that generates motion of the cochlea fluid. Such auditory prostheses include, for example, acoustic hearing aids, bone conduction devices, and direct acoustic stimulators.

In many people who are profoundly deaf, however, the reason for their deafness is sensorineural hearing loss. Those suffering from some forms of sensorineural hearing loss are unable to derive suitable benefit from auditory prostheses that generate mechanical motion of the cochlea fluid. Such individuals can benefit from implantable auditory prostheses that stimulate nerve cells of the recipient's auditory system in other ways (e.g., electrical, optical and the like). Cochlear implants are often proposed when the sensorineural hearing loss is due to the absence or destruction of the cochlea hair cells, which transduce acoustic signals into nerve impulses. Auditory brainstem stimulators might also be proposed when a recipient experiences sensorineural hearing loss due to damage to the auditory nerve.

SUMMARY

In one aspect an implantable hearing system is provided. The implantable hearing system comprises at least one implant module configured to be implanted in a recipient, and an implantable coil configured to form a radio-frequency link with an external coil. The implantable coil is configured to be implanted in the recipient at a location that is distal to the at least one implant module.

In another aspect of the present invention, a cochlear implant is provided. The cochlear implant comprises a stimulator unit configured to be implanted within a recipient's mastoid, a stimulating assembly electrically connected to the stimulator unit and configured to be implanted in a recipient's cochlea, and an implantable tympanic membrane coil electrically connected to the stimulator unit and configured to be implanted in a recipient's middle ear cavity adjacent to the recipient's tympanic membrane to form a trans-tympanic radio-frequency link with an external coil positioned in the recipient's ear canal.

In a further aspect, an implantable hearing system is provided. The implantable hearing system comprises at least one implant module configured to be implanted in a recipient, and an implantable tympanic membrane coil electrically connected to the at least one implant module and comprised of fabiform-shaped wire turns.

BRIEF DESCRIPTION OF THE DRAWINGS

Embodiments of the present invention are described herein in conjunction with the accompanying drawings, in which:

FIG. 2B is a block diagram of the implanted portions of the distributed implantable hearing system of FIG. 2A;

FIG. 4B is a block diagram of the implanted portions of the distributed implantable hearing system of FIG. 4A;

DETAILED DESCRIPTION

Presented herein are distributed implantable hearing systems that have at least a main implant module that is physically separated from a distally positioned inner radio-frequency (RF) coil. Embodiments presented herein may include a main implant module positioned within a recipient's mastoid and an implantable coil positioned within a recipient's middle ear cavity.

For ease of illustration, embodiments are primarily described herein with reference to a distributed implantable hearing system in the form of a cochlear implant. However, it is to be appreciated that the techniques presented herein may be used with other implantable hearing systems including, for example, auditory brainstem stimulators, direct acoustic stimulators, bone conduction devices, etc.

Figure 1:
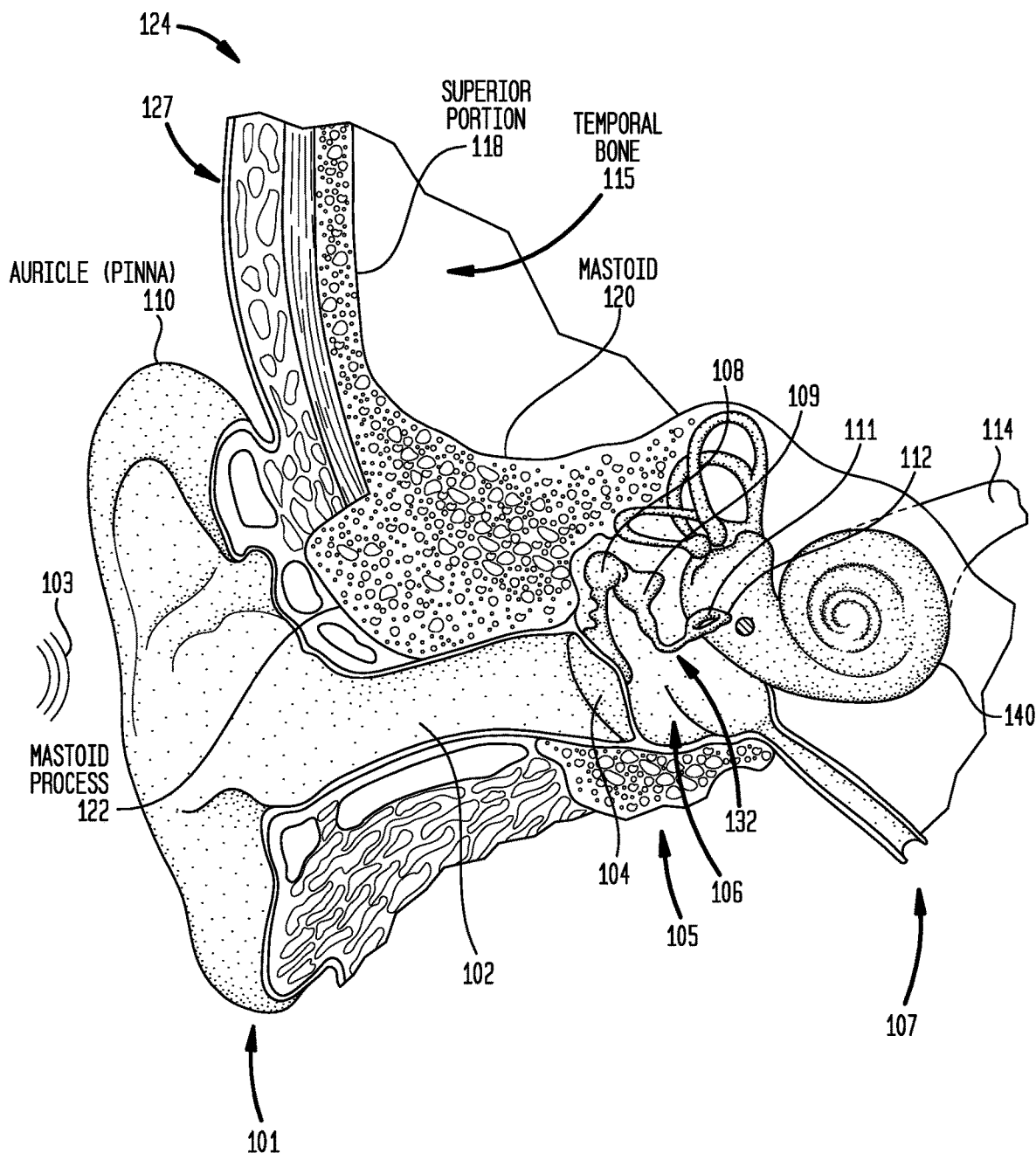
FIG. 1 is a schematic diagram illustrating the anatomy of a recipient at a location in which a distributed implantable hearing system in accordance with embodiments presented herein may be implanted.

Before describing illustrative embodiments of the distributed implantable hearing systems, a brief description of the human anatomy in the region of a recipient's ear is first provided with reference to FIG. 1. As shown, a human ear generally includes an outer ear 101, a middle ear 105, and an inner ear 107. In a fully functional ear, outer ear 101 comprises an auricle 110 and an ear canal (auditory canal) 102. An acoustic pressure or sound wave 103 is collected by auricle 110 and channeled into and through ear canal 102. Disposed across the distal end of ear cannel 102 is a tympanic membrane 104 which vibrates in response to sound wave 103. This vibration is coupled to oval window or fenestra ovalis 112 through three bones of middle ear 105, collectively referred to as the ossicular chain or ossicles 132. The three bones of the ossicular chain 132 are: the malleus 108, which is attached to the tympanic membrane 104; the stapes 111, which is attached to the recipient's oval window 112; and the incus 109, which connects the stapes 111 to the malleus 108. Bones 108, 109 and 111 are disposed in a middle ear cavity 106 and serve to filter and amplify sound wave 103, causing oval window 112 to articulate/vibrate in response to vibration of tympanic membrane 104. This vibration of the oval window 112 sets up waves of fluid motion of the perilymph within cochlea 140. Such fluid motion, in turn, activates tiny hair cells (not shown) inside of cochlea 140. Activation of the hair cells causes appropriate nerve impulses to be generated and transferred through the spiral ganglion cells (not shown) and auditory nerve 114 to the brain (also not shown) where they are perceived as sound The human skull is formed from a number of different bones that support various anatomical features and that form the brain cavity. Illustrated in FIG. 1 is the temporal bone 115 which is situated at the side and base of the recipient's skull 124. For ease of reference, the temporal bone 115 is referred to herein as having a superior portion 118 and a mastoid portion 120. The superior portion 118 comprises the section of the temporal bone 115 that extends superior to the auricle 110. That is, the superior portion 118 is the section of the temporal bone 115 that forms the side surface of the skull. The mastoid portion 120, referred to herein simply as the mastoid 120, is positioned inferior to the superior portion 118. The mastoid 120 is the section of the temporal bone 115 that surrounds the middle ear 105. The mastoid 120 includes the mastoid process 122 (i.e., a conical prominence projecting from the undersurface of the mastoid 122 behind a central region of the auricle 110).

Conventional cochlear implants use a radio-frequency (RF) link to transcutaneously transfer (i.e., transfer through the recipient's skin) power and data to the implanted components. To enable this transcutaneous transfer, conventional cochlear implants include an implantable coil positioned underneath the skin adjacent to a subcutaneous outer surface of the recipient's skull. The subcutaneous outer surface of the recipient's skull (i.e., the outer surface of the skull underneath the recipient's skin and tissue) is referred to herein as the skull exterior 127. Stated differently, a component positioned at a recipient's skull exterior 127 is positioned adjacent to the skull bone, but underneath the recipient's skin and tissue.

The implantable coils positioned at the skull exterior 127 are co-located with a stimulator/receiver unit that is also positioned underneath the skin adjacent to the outer surface of the recipient's skull. The stimulator/receiver unit is typically positioned in a surgically created pocket at the outer surface of the superior portion 118 of the temporal bone 115.

The implantable coil communicates with a corresponding external coil that is configured to be positioned on the outer surface of the recipient's skin adjacent to the implantable coil. The implantable coil and the external coil are aligned with one another via corresponding magnets. That is, the implantable coil and the external coil are each disposed around magnets that are configured to magnetically mate with one another.

These conventional transcutaneous systems have several disadvantages. For example, the use of an external coil is easily visible and identifies the recipient as a cochlear implant user. Additionally, the need for the implantable magnet to retain the external coil in place on the recipient's head causes problems during a Magnetic Resonance Imaging (MRI) scan. In particular, the magnetic fields generated during an MRI scan can impart translation forces (torque) on an implanted magnet. Torque occurs because the poles of the implanted magnet attempt to align with the applied magnetic field. This torque can cause discomfort, pain, damage to the device containing the magnet, and/or damage to the surrounding tissue. As such, during an MRI scan, the implanted magnet may need to be removed or stabilized using an external bandage.

The implanted magnet may also generate artifacts during the MRI scan that affect the quality of the scan. Furthermore, during an MRI scan, the implanted magnet may become demagnetized.

Figure 2A:
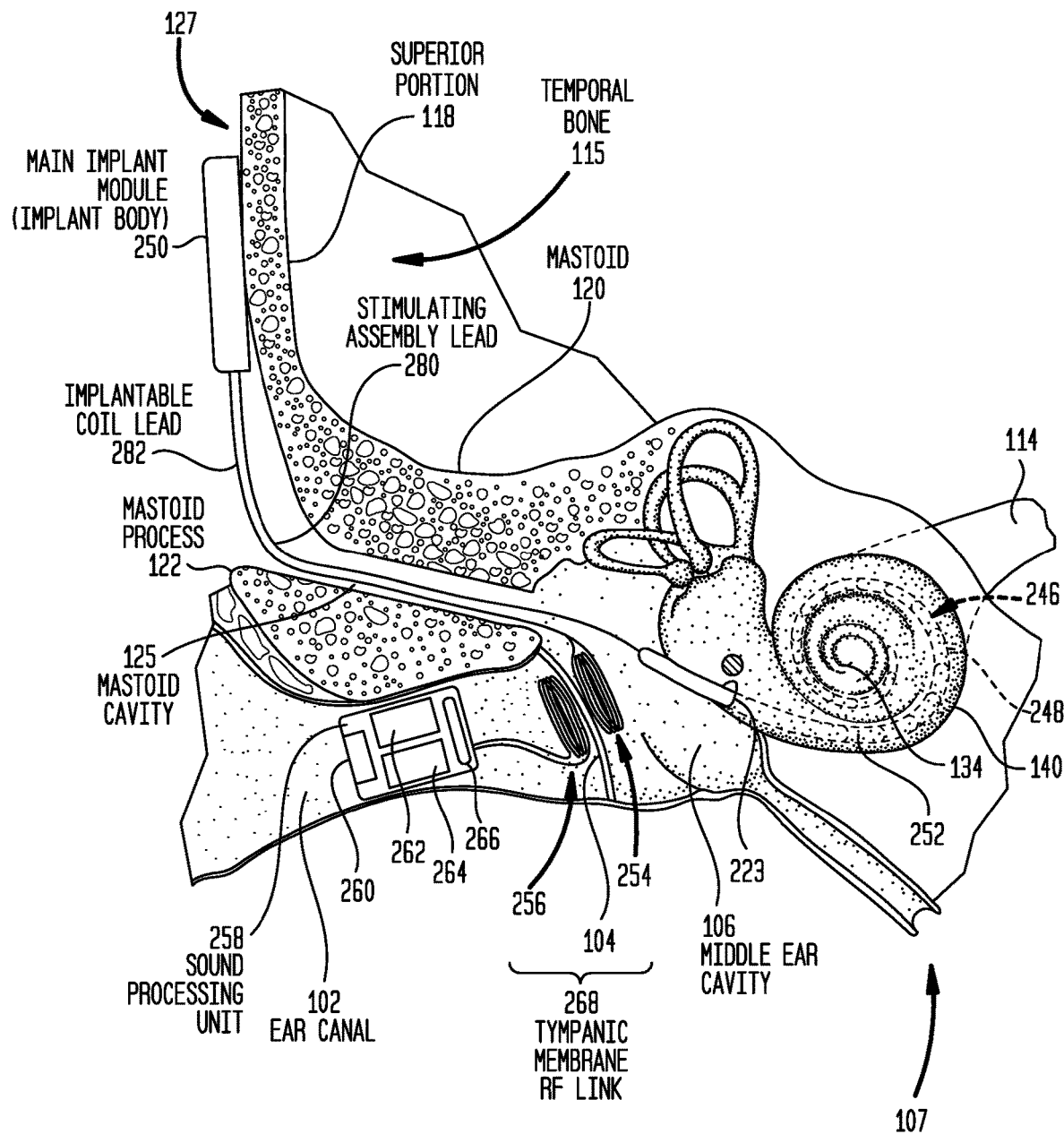
FIG. 2A is a schematic diagram illustrating a distributed implantable hearing system in accordance with embodiments presented herein implanted in a recipient.

Presented herein are distributed hearing system (e.g., cochlear implant) architectures that eliminate the need for an external coil that is worn on the recipient's head as well as the requirement for an implantable magnet. FIG. 2A is a schematic diagram of a first cochlear implant 200 having a distributed architecture in accordance with embodiments presented herein. Cochlear implant 200 is shown implanted in the human anatomy illustrated in FIG. 1. For ease of illustration, the ossicular chain 132 has been omitted from FIG. 2A. However, as described further below, the ossicular chain 132 may be present in certain embodiments. FIG. 2B is a block diagram of the implantable components of cochlear implant 200.

Cochlear implant 200 comprises a main implant module (implant body) 250, an elongate stimulating assembly 252, an implantable (inner) coil 254, a non-implanted (outer) coil 256, and a sound processing unit 258. The sound processing unit 258 is an in-the-ear unit that is configured to be partially or fully positioned in a recipient's ear canal 102. The sound processing unit 258 includes, or is connected to, one or more sound input elements 260 (e.g., microphones, telecoils, etc.) for detecting sound. The sound processing unit 258 also includes a sound processor 262 that is configured to convert electrical signals generated by the sound input element(s) 260 into coded data signals. The sound processing unit 258 may also include a power supply (e.g., battery) 264 and a transceiver unit 266. The transceiver unit 266 is configured to provide power signals (from the power source 264) and coded data signals (from the sound processor 262) to the outer coil 256.

As shown, the outer coil 256 is a radio-frequency (RF) wire antenna coil comprised of multiple turns of electrically insulated single-strand or multi-strand wire (e.g., platinum or gold wire). The outer coil 256 is sized and shaped so as to be positioned within the recipient's ear canal adjacent to an outer (exterior) surface of the tympanic membrane 104. The implantable coil 254 also is an RF wire antenna coil comprised of multiple turns of electrically insulated single-strand or multi-strand wire (e.g., platinum or gold wire). The implantable coil 254 is sized and shaped so as to be positioned in the recipient's middle ear cavity 106 adjacent to an inner (internal) surface of the tympanic membrane 104. More specifically, the outer coil 256 and the implantable coil 254 are positioned so as to be inductively coupled to one another across the tympanic membrane 104. In this arrangement on opposing sides of the tympanic membrane 104, the outer coil 256 and the implantable coil 254 collectively form a trans-tympanic membrane RF link 268.

In certain embodiments, the outer coil 256 has a plurality of turns that are dimensioned so as to have an outer diameter that is approximately the same as, or slightly larger than, a diameter of the ear canal adjacent to the tympanic membrane 104. In such embodiments, the inner surface of the ear canal operates to slightly compress the turns of the outer coil 256 to retain the outer coil in position adjacent to tympanic membrane 104. In the same or other embodiments, the outer coil 256 may be held in place adjacent to the tympanic membrane 104 using standard surgical techniques such as sutures or an adhesive. The outer coil 256 may also be held in place by the ear canal compressing against the case containing the external electronics or by some plug mechanism fitted to the outer ear. The implantable coil 254 may further be held in place adjacent to the tympanic membrane 104 using standard surgical techniques such as sutures or an adhesive. In certain embodiments described further below, the implantable coil 254 may have a specific shape that preserves the structure of the ossicular chain 132.

As shown, the positions of the outer coil 256 and the implantable coil 254 are controlled by the recipient's anatomy and no magnets are utilized to retain the coils in position. As such, the trans-tympanic membrane RF link 268 has improved MRI compatibility over transcutaneous coil arrangements.

As noted above, transcutaneous RF links utilize inductive transfer across a skin/tissue flap. As such, in transcutaneous links the external and implantable coil may be separated by a distance of up to approximately 12 millimeters (mm) due to the presence of the skin, muscle, fat, and/or other tissue (i.e., the coils are separated by a skin flap of 12 mm). This separation requires the use of relatively large external and implantable coils with relatively large power requirements. For example, a typical cochlear implant system may include coils having a diameter of approximately 30 mm with a 12 mm diameter magnet in the center. The magnet reduces efficiency as it is conductive. The typical power requirement of an implantable component is approximately 10 milliwatts (mW), but the coil is only 25% efficient under ideal conditions. As such, under the ideal conductions, 40 mW is supplied to the external coil which, at an efficiency of 25%, results in the supply of 10 mW to the implantable component. As the separation of the external and implantable coils increases, the efficiency decreases. In one arrangement, the efficiency is approximately 10% at a 12 mm spacing (i.e., with a 12 mm skin flap). Such arrangements require 100 mW delivered to the external coil to supply 10 mW to the implantable component. A separation that is too great may prevent sufficient power from crossing the link to power the implantable component. To support the widest range of skin flap thicknesses, the operation of the external coil is optimized for a middle thickness of typically 6 mm. The efficiency will reduce for both thinner and thicker skin flaps. Initially, this means a shorter battery life and, if the separation is too extreme, the device stops functioning. Additionally, this may result in the use of coils that may be overly large for certain recipients.

In contrast, the tympanic membrane 104 is relatively thin with a substantially uniform thickness for all recipients. As such, the outer coil 256 and the implantable coil 254 have an implanted separation of approximately 1-2 mm. Due to this small coil separation, the outer coil 256 and the implantable coil 254 may be substantially smaller than the coils used in transcutaneous arrangements. Similarly, less current may be required to transfer power and data between the outer coil 256 and the implantable coil 254 than is required in transcutaneous arrangements. For example, the outer coil 256 and the implantable coil 254 in the trans-tympanic membrane RF link 268 may each have a diameter of approximately 6 mm that need not be disposed around a magnet. With a known and constrained coil separation (resulting from the substantially uniform thickness of the tympanic membrane 104) the tympanic membrane RF link 268 can be optimized for high efficiency operation over a thickness of, for example, 1.5 mm. The use of smaller diameter coils relative to transcutaneous arrangements means that the wire is shorter so there will be less resistive losses. This results in a higher Q factor and thus higher efficiency coils. The consistent coil separation means that the same efficiency will be available to all recipients.

As shown in FIG. 2B, the main implant module 250 comprises a rechargeable power supply 270, a stimulator unit 272, and an internal receiver/transmitter unit 274 (sometimes referred to herein as transceiver unit 274). Due to the presence of the transceiver unit 274 and the stimulator unit 272, main implant module 250 is sometimes referred to herein as a stimulator/transceiver unit 250. It is to be appreciated that the main implant module 250 may include other components to facilitate operation of the cochlear implant 200. However, merely for ease of illustration, these additional components have been omitted from FIG. 2B.

The main implant module 250 also comprises a hermetically sealed housing (case) 276 that includes a feedthrough 278 extending through the housing. As shown in FIG. 2A, the main implant module 250 is configured to be positioned adjacent to an outer surface of the recipient's temporal bone 115, for example, adjacent to the superior portion 118. In this location at the skull exterior 127, the main implant module 250 is directly beneath the recipient's tissue and the main implant module is subject to external stresses (e.g., impacts). As such, the housing 276 is a robust element that is specifically designed to protect the internal components (e.g., stimulator unit 272, transceiver unit 274, power supply 270, etc.) from impacts or other external stresses. For example, a typical implant housing of approximately 25 mm square made of a material such as ceramic is likely to break when subject to an industry standard (EN45502-2-3) worse case impact of 2.5 Joules (J) with a steel hammer. However, a sufficiently thick outer shell (greater than, for example, 1 mm) of titanium may resist an impact of this same magnitude. Otherwise, the addition of pillars or other strengthening members is required to achieve the required robustness. As such, in certain examples the housing may be formed from titanium.

The elongate stimulating assembly 252 is at least partially implanted in cochlea 140 and includes a contact array 246 comprising a plurality of stimulating contacts 248. Contact array 246 may comprise electrical contacts and/or optical contacts.

Stimulating assembly 252 extends through cochleostomy 223 and has a proximal end connected to main implant module 250 via stimulating assembly lead (cable) 280 that extends through a surgically formed cavity 125 in mastoid 120. More specifically, to insert the stimulating assembly 252 into cochlea 140, a surgeon drills an opening through the mastoid process 122 and mastoid 120 to reach the middle ear cavity 106. The stimulating assembly 252 is inserted through the mastoid cavity 125 and through middle ear cavity 106 into cochlea 140. At the end of the surgical implantation, stimulating assembly lead 280 is positioned in, and extends through, the mastoid cavity 125 and the middle ear cavity 106. The stimulating assembly lead 280 may include a plurality of electrically insulated conductors (wires).

As noted, the implantable coil 254 is positioned in the middle ear cavity 106. As such, the implantable coil 254 is referred to herein as being distally positioned to the main implant module 250. That is, implantable coil 254 is physically separate from, and positioned at a distance from, the main implant module 250. In fact, in the embodiment of FIG. 2A, the main implant module 250 and the implantable coil 254 are positioned in different anatomical regions of the recipient's skull (i.e., the main implant module 250 is positioned at an external surface of the recipient's skull while the implantable coil 254 is positioned within the middle ear cavity 106.

Similar to the stimulating assembly 252, the implantable coil 254 is electrically connected to the main implant module 250 via a lead (cable) 282, referred to herein as the implantable coil lead 282. In one embodiment, the implantable coil 254 is inserted through the mastoid cavity 125 and into middle ear cavity 106 where it is secured adjacent to the tympanic membrane 104. At the end of the surgical implantation, the implantable coil lead 282 is positioned in, and extends through, the mastoid cavity 125 and the middle ear cavity 106. The implantable coil lead 282 may include a plurality of electrically insulated conductors (wires).

As shown, the stimulating assembly lead 280 and the implantable coil lead 282 electrically connect separate components (i.e., the stimulating assembly 252 and the implantable coil 254) to the main implant module 250. The feedthrough 278 is configured to provide electrically independent, hermetically sealed connections for each of the stimulating assembly lead 280 and the implantable coil lead 282 through the housing 276. That is, the feedthrough 278 is configured to provide multiple independent groups of connections, where one group is associated with the stimulating assembly lead 280 and one group is associated with the implantable coil lead 282.

In operation, power and/or data is transferred from the outer coil 256 through the tympanic membrane 104 to implantable coil 254. As shown in FIG. 2B, electrical signals 229 corresponding to the power/data are sent from the implantable coil 254 along implantable coil lead 282 to transceiver unit 274 in main implant module 250. Power signals may be used to charge power supply 270, while data signals are used by stimulator unit 272 to generate stimulation signals 231 that are provided to stimulating assembly 252 via stimulating assembly lead 252. The stimulation signals 231 are then delivered to the recipient via the stimulating contacts 248.

Figure 3A:
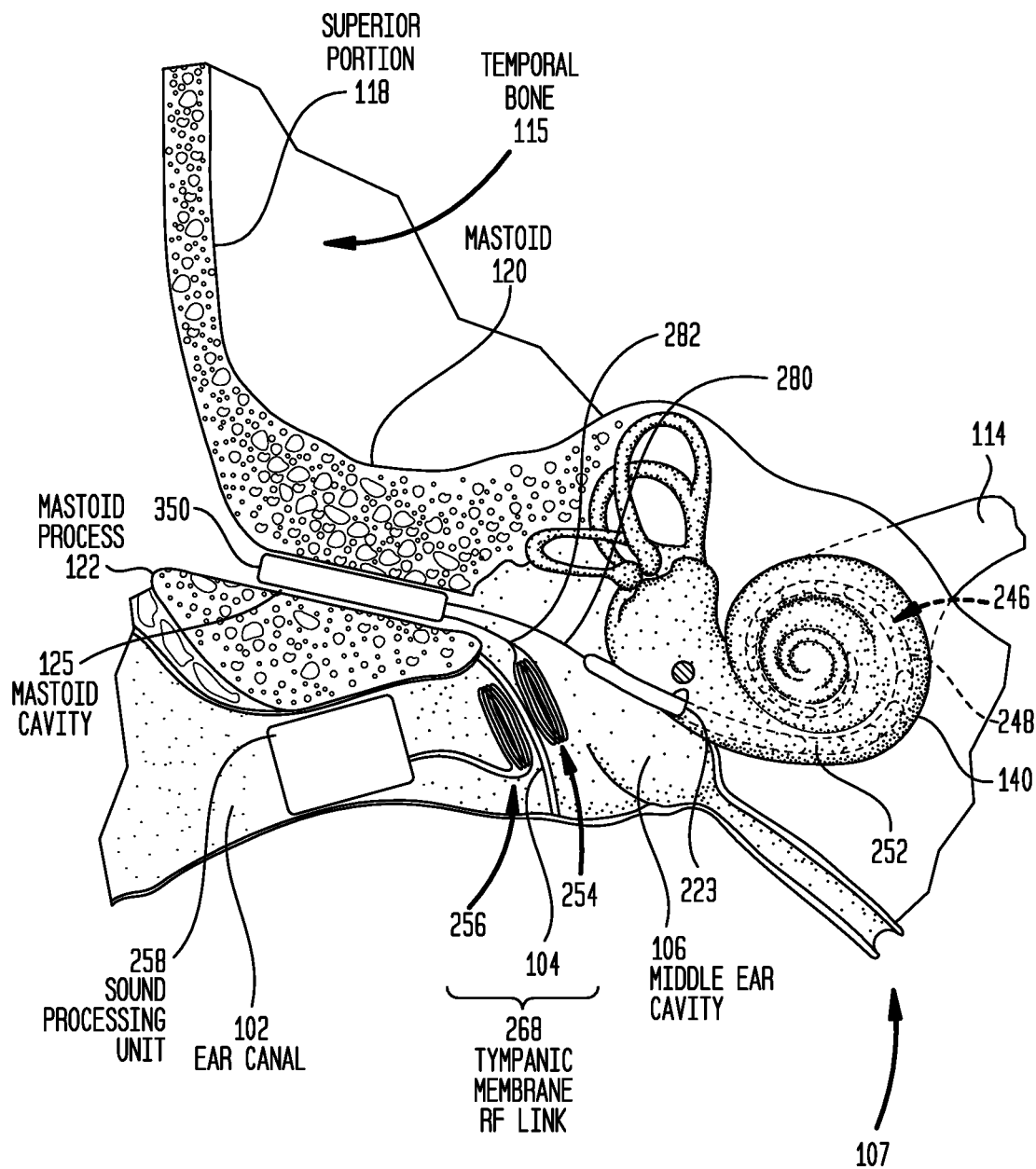
FIG. 3A is a schematic diagram illustrating a distributed implantable hearing system in accordance with embodiments presented herein implanted in a recipient.
Figure 3B:
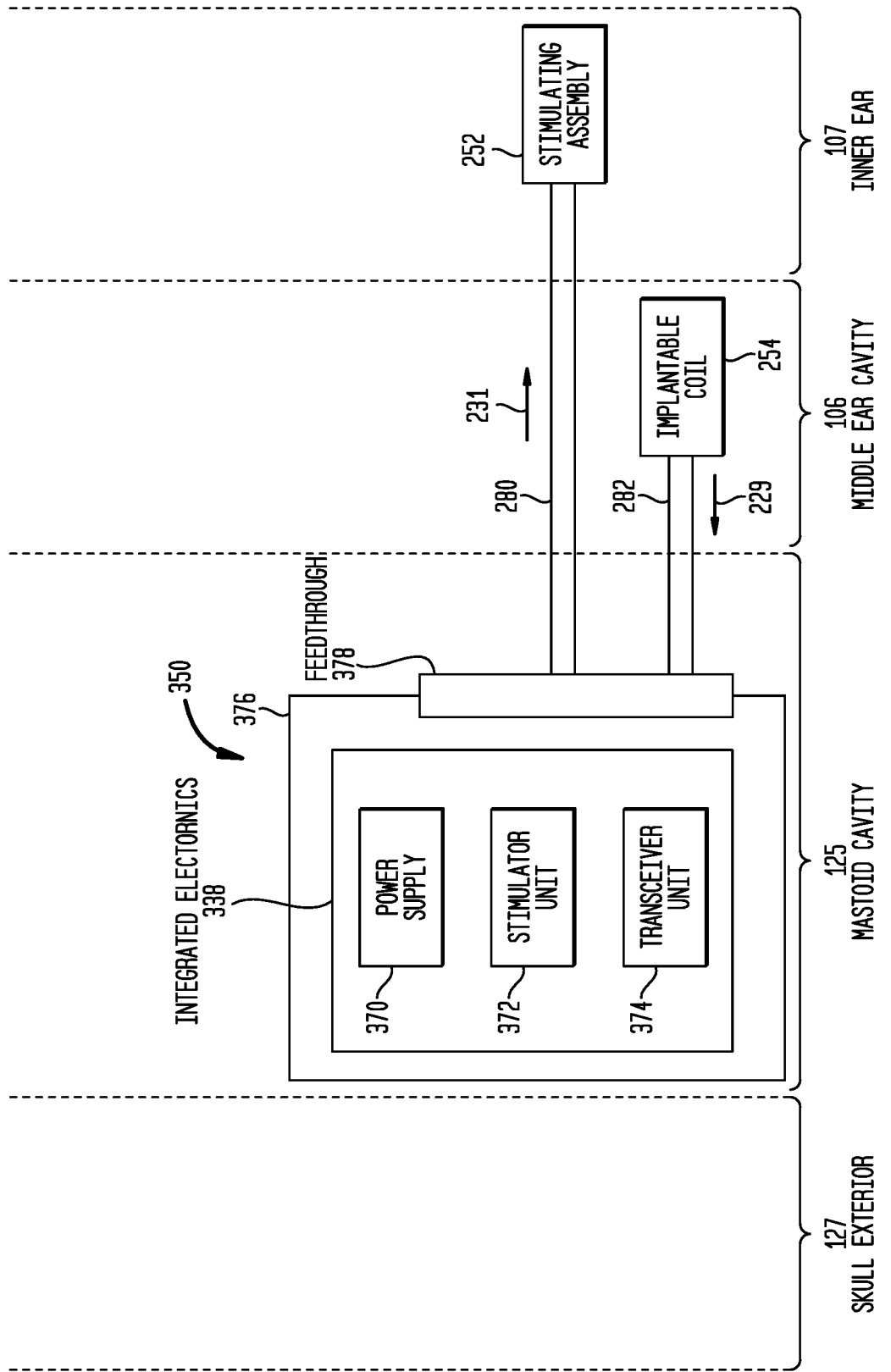
FIG. 3B is a block diagram of the implanted portions of the distributed implantable hearing system of FIG. 3A.

FIGS. 2A and 2B illustrate an embodiment where the main implant module 250 is positioned at the skull exterior 127. As noted above, the positioning of a component at the skull exterior 127 requires that the component include (or be positioned in) a robust housing that is designed to protect the component from external stresses, such as impacts. FIGS. 3A and 3B illustrate an arrangement where a robust housing is not required to protect any components from impact. The use of a robust housing is eliminated by ensuring that no components are positioned at the skull exterior 127.

More specifically, FIG. 3A is a schematic diagram of a cochlear implant 300 having a distributed architecture in accordance with embodiments presented herein that does not utilize a robust housing to protect components from external stresses. Cochlear implant 300 is shown implanted in the human anatomy illustrated in FIG. 1. For ease of illustration, the ossicles 132 have been omitted from FIG. 3A. However, as described further below, the ossicular chain 132 may be present in certain embodiments. FIG. 3B is a block diagram of the implantable components of cochlear implant 300.

Cochlear implant 300 comprises a main implant module (implant body) 350, the elongate stimulating assembly 252, the implantable coil 254, the outer coil 256, and the sound processing unit 258. As described above with reference to FIG. 2A, the sound processing unit 258 is an in-the-ear unit that is configured to be partially or fully positioned in a recipient's ear canal 102. For ease of illustration, the components of sound processing unit 258 have been omitted from FIG. 3A.

The outer coil 256 and the implantable coil 254 have substantially the same configuration as described above with reference to FIG. 2A so as to collectively form the transtympanic membrane RF link 268. Similarly, the elongate stimulating assembly 252 is, as described above, at least partially implanted in cochlea 140.

As shown in FIG. 3B, the main implant module 350 comprises a rechargeable power supply 370, a stimulator unit 372, and an internal receiver/transmitter unit 374, sometimes referred to herein as transceiver unit 374. Due to the presence of the stimulator unit 372 and the transceiver unit 374, main implant module 350 is sometimes referred to herein as a stimulator/transceiver unit 350. It is to be appreciated that the main implant module 350 may include other components to facilitate operation of the cochlear implant 300. However, merely for ease of illustration, these additional components have been omitted from FIG. 3B.

The main implant module 350 also comprises a hermetically sealed housing (case) 376 that includes a feedthrough 378 extending through the housing. As shown in FIG. 3A, the main implant module 350 is fully recessed within the mastoid cavity 125. That is, the main implant module 350 has a size and shape so as to be entirely positioned within the mastoid cavity 125. In this location, the main implant module 350 is recessed within the recipient's mastoid 120. Because the main implant module 350 is recessed within the mastoid 120, the mastoid effectively protects the main implant module 350 from external stresses (e.g., impacts). As such, the housing 376 need not be a robust element designed to protect the internal components (e.g., stimulator unit 372, transceiver unit 374, power supply 370, etc.) from impacts or other external stresses. For example, in the event of a standard worst case impact of 2.5 J with a steel hammer, the impact will be distributed into the skull. While an impact of this energy will cause pain or discomfort, it is unlikely to permanently damage normal healthy bone. No direct impact is transferred to the implant. At worst, some vibration will be transferred to the implant. This is easily withstood by a thin (0.2 mm) titanium enclosure or even by a ceramic enclosure. As such, the addition of strengthening members to the main implant module 350 is not required.

In certain embodiments, the housing 376 may be a thin titanium shell and the feedthrough 378 may be formed from a ceramic material that is attached to the titanium shell via, for example, brazing. In alternative embodiments, the housing 376 and feedthrough 378 may both be formed from a ceramic material (i.e., the main implant module 350 includes a fully ceramic housing).

It is known that ceramic materials are superior electrical insulators and are impervious to fluid ingress. Although ceramic materials are relatively hard, ceramic materials are also brittle. As a result, ceramic materials are not robust or well suited for use as a housing designed to protect components from external stresses. However, as detailed above, in the arrangement of FIGS. 3A and 3B, the recessed main implant module 350 is protected from external stresses by the mastoid 120 (i.e., recessed in mastoid cavity 125). As such, the implanted location for the main implant module 350 enables the use of a fully ceramic housing which could not be used in an arrangement where the main implant module is located at the skull exterior (i.e., there is a danger a ceramic housing at the skull exterior 127 could break, resulting in catastrophic device failure).

In further embodiments, the main implant module 350 includes a housing 376 that is formed from a moldable ceramic material. In such embodiments, the housing 376 could be formed into a variety of shapes. The shape of the mastoid cavity varies widely from recipient to recipient based on individual anatomy. It is an irregular shape that in certain cases approximates a triangular prism. In certain examples, the maximum dimensions are 2 or 3 centimeters (cm) per side, but not all the space is useable. The ability to form complex shapes means the maximum useable volume can be utilized. Alternately more than one shape could be supplied and the surgeon selects the best shape to fit a specific anatomy.

The use of a non-robust housing facilitates a reduction in the size of the main implant module 350 relative to arrangements where a main implant module is located at the skull exterior (e.g., the housing may be thinner, formed into smaller shapes, etc.). However, further inventive aspects may also be utilized to create a reduced size main implant module 350 that is located entirely within the mastoid cavity 125. For example, one additional inventive aspect that facilitates a reduced sized main implant module 350 is the use of an integrated approach in the design of the electrical components within the main implant module 350. More specifically, the main implant module 350 may be designed through the use of a high level Application-Specific Integrated Circuit (ASIC) integration approach that minimizes the use of discrete components. This integrated ASIC approach results in a single integrated electronics package 338 that includes all of the electrical components (e.g., the power supply 370, stimulator unit 372, and transceiver unit 374). The integrated ASIC approach and/or other approaches described above effectively miniaturize the electrical components within main implant module 350, relative to conventional arrangements, thereby facilitating the reduced size main implant module 350.

In addition to the use of ASICs to minimize electrical component count, a range of miniaturization techniques may be utilizes to manufacture a device of the dimensions needed to be implanted within the mastoid cavity. For example, space efficient connections from the ASIC and limited other components are utilized. This could be achieved using wire bonding to a Printed Circuit Board (PCB) or preferable directly to the feedthrough. Additionally, systematic elimination of components is utilized. The PCB can be eliminated by direct connection of electrical components to each other and to a specially designed feedthrough. Furthermore, external connections (e.g., small crimps or wire bonds) of the coil and stimulator assembly lead to the feedthrough are made space efficient. The housing is formed to as to be a close fit around the component volume. As previously described, this close fit of the housing could be achieved using a moldable ceramic. Alternatively, this close fit could be achieved in titanium using drawing technologies or metal additive technologies such as metal injection molding (MIM). If a reference electrode is required, this reference electrode can be formed from the titanium case to further reduce the size of the module.

Stimulating assembly 252 is connected to main implant module 350 via stimulating assembly lead 280 that is positioned in, and extends through, the middle ear cavity 106 and possibly a section the mastoid cavity 125, depending on the final position of the main implant module 350. The stimulating assembly lead 280 may include a plurality of electrically insulated conductors (wires).

As noted, the implantable coil 254 is positioned in the middle ear cavity 106. As such, the implantable coil 254 is referred to herein as being distally positioned to the main implant module 350. That is, implantable coil 254 is physically separate from, and positioned at a distance from, the main implant module 350. In fact, in the embodiment of FIGS. 3A and 3B, the main implant module 350 and the implantable coil 254 are positioned at different anatomical regions of the recipient's skull (i.e., the main implant module 350 is positioned in the mastoid cavity 125 while the implantable coil 254 is positioned within the middle ear cavity 106).

The implantable coil 254 is electrically connected to the main implant module 350 via the implantable coil lead 282. In one embodiment, the implantable coil 254 is inserted through the mastoid cavity 125 and into middle ear cavity 106 where it is secured adjacent to the tympanic membrane 104. At the end of the surgical implantation, the implantable coil lead 282 is positioned in, and extends through, the middle ear cavity 106 and possibly a section the mastoid cavity 125, depending on the final position of the main implant module 350. The implantable coil lead 282 may include a plurality of electrically insulated conductors (wires).

As shown, the stimulating assembly lead 280 and the implantable coil lead 282 electrically connect separate components (i.e., the stimulating assembly 252 and the implantable coil 254) to the main implant module 350. The feedthrough 378 is configured to provide independent, hermetically sealed connections for each of the stimulating assembly lead 280 and the implantable coil lead 282 through the housing 376. That is, the feedthrough 378 is configured to provide multiple independent groups of connections, where one group is associated with the stimulating assembly lead 280 and one group is associated with the implantable coil lead 282.

In operation, power and/or data is transferred from the outer coil 256 through the tympanic membrane 104 to implantable coil 254. As shown in FIG. 3B, electrical signals 229 corresponding to the power/data are sent from the implantable coil 254 along implantable coil lead 282 to transceiver unit 374 in main implant module 350. Power signals may be used to charge power supply 370, while data signals are used by stimulator unit 372 to generate stimulation signals 231 that are provided to stimulating assembly 252 via stimulating assembly lead 252. The stimulation signals 231 are then delivered to the recipient via the stimulating contacts 248.

Figure 4A:
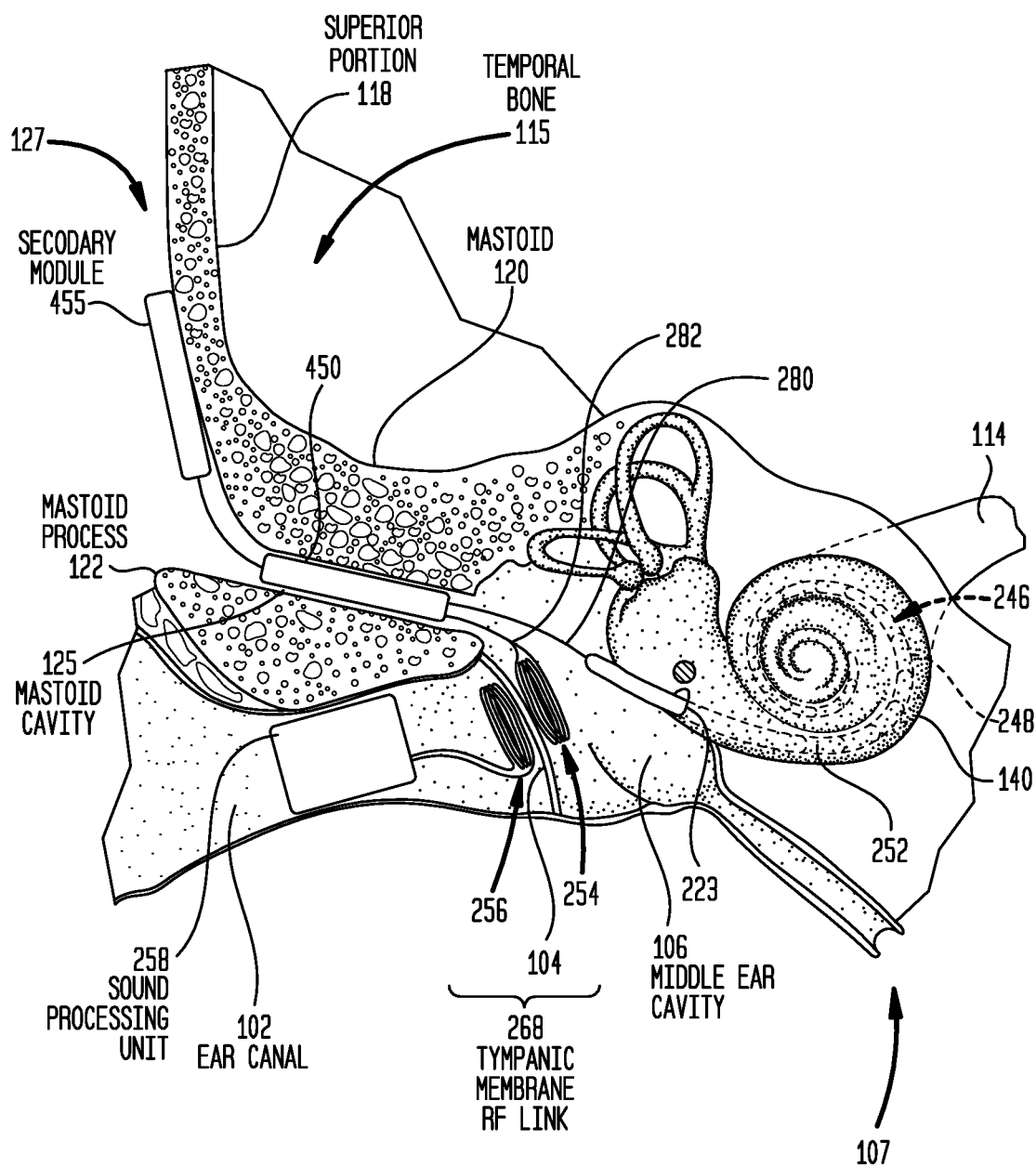
FIG. 4A is a schematic diagram illustrating a distributed implantable hearing system in accordance with embodiments presented herein implanted in a recipient.

FIGS. 4A and 4B illustrate a distributed architecture where multiple implantable modules are used in conjunction with a trans-tympanic membrane RF link. More specifically, FIG. 4A is a schematic diagram of a cochlear implant 400 shown implanted in the human anatomy illustrated in FIG. 1. For ease of illustration, the ossicles 132 have been omitted from FIG. 4A. However, as described further below, the ossicular chain 132 may be present in certain embodiments. FIG. 4B is a block diagram of the implantable components of cochlear implant 400.

Cochlear implant 400 comprises a main implant module (implant body) 450, a secondary module (auxiliary or upgrade module) 455, the elongate stimulating assembly 252, the implantable coil 254, the outer coil 256, and a sound processing unit 258. As described above with reference to FIG. 2A, the sound processing unit 258 is an in-the-ear unit that is configured to be partially or fully positioned in a recipient's ear canal 102. For ease of illustration, the components of sound processing unit 258 have been omitted from FIG. 4A.

The outer coil 256 and the implantable coil 254 have substantially the same configuration as described above with reference to FIG. 2A so as to collectively form the transtympanic membrane RF link 268. Similarly, the elongate stimulating assembly 252 is, as described above, at least partially implanted in cochlea 140.

As shown in FIG. 4B, the main implant module 450 comprises a stimulator unit 472 and an internal receiver/transmitter unit 474, sometimes referred to herein as transceiver unit 474. Due to the presence of the stimulator unit 472 and the transceiver unit 474, main implant module 450 is sometimes referred to herein as a stimulator/transceiver unit 450. It is to be appreciated that the main implant module 450 may include other components to facilitate operation of the cochlear implant 400. However, merely for ease of illustration, these additional components have been omitted from FIG. 4B.

The main implant module 450 also comprises a hermetically sealed housing (case) 476 that includes a feedthrough 478 extending through the housing. As shown in FIG. 4A, the main implant module 450 is fully recessed within the mastoid cavity 125. That is, the main implant module 450 has a size and shape so as to be entirely positioned within the mastoid cavity 125. In this location, the main implant module 450 is recessed within the recipient's mastoid 120. Because the main implant module 450 is recessed within the mastoid 120, the mastoid effectively protects the main implant module 450 from external stresses (e.g., impacts). As such, similar to housing 376 of main implant module 350 in FIGS. 3A and 3B, the housing 476 need not be a robust element designed to protect the internal components. The housing 476 may have the same or substantially similar arrangement as the housing 376 of FIGS. 3A and 3B (e.g., ceramic feedthroughs with a thin titanium shell, a fully ceramic housing, a housing formed from a moldable ceramic, different shapes, etc.)

The use of a non-robust housing facilitates a reduction in the size of the main implant module 450 relative to arrangements where a main implant module is located at the skull exterior. However, similar to the embodiment of FIGS. 3A and 3B, further inventive aspects may also be utilized to create the recessed main implant module 450 that is located entirely within the mastoid cavity 125. For example, a high level ASIC integration approach that minimizes the use of discrete components may be used to generate an integrated electronics package 438 that includes all of the electrical components (e.g., the stimulator unit 472 and transceiver unit 474). The integrated ASIC approach and/or other approaches described above effectively miniaturize the electrical components within main implant module 450, relative to conventional arrangements, thereby facilitating a smaller main implant module 450.

Stimulating assembly 252 is connected to main implant module 450 via stimulating assembly lead 280 that is positioned in, and extends through, the middle ear cavity 106 and possibly a section the mastoid cavity 125, depending on the final position of the main implant module 450. The stimulating assembly lead 280 may include a plurality of electrically insulated conductors.

As noted, the implantable coil 254 is positioned in the middle ear cavity 106. As such, the implantable coil 254 is referred to herein as being distally positioned to the main implant module 450. That is, implantable coil 254 is physically separate from, and positioned at a distance from, the main implant module 450. In fact, in the embodiment of FIGS. 4A and 4B, the main implant module 450 and the implantable coil 254 are positioned in different anatomical regions of the recipient's skull (i.e., the main implant module 450 is positioned in the mastoid cavity 125 while the implantable coil 254 is positioned within the middle ear cavity 106).

The implantable coil 254 is electrically connected to the main implant module 450 via the implantable coil lead 282. In one embodiment, the implantable coil 254 is inserted through the mastoid cavity 125 and into middle ear cavity 106 where it is secured adjacent to the tympanic membrane 104. At the end of the surgical implantation, the implantable coil lead 282 is positioned in, and extends through, the middle ear cavity 106 and possibly a section the mastoid cavity 125, depending on the final position of the main implant module 450. The implantable coil lead 282 may include a plurality of electrically insulated conductors.

As shown, the main implant module 450 includes a first feedthrough 478(1) and a second feedthrough 478(2). In certain embodiments, feedthroughs 478(1) and 478(2) may be integrated as a single feedthrough.

The stimulating assembly lead 280 and the implantable coil lead 282 electrically connect separate components (i.e., the stimulating assembly 252 and the implantable coil 254) to the main implant module 450 via feedthrough 478(1). The feedthrough 478(1) extends through housing 476 so as to provide independent, hermetically sealed connections for each of the stimulating assembly lead 280 and the implantable coil lead 282 through the housing 476. That is, the feedthrough 478(1) is configured to provide multiple independent groups of connections, where one group is associated with the stimulating assembly lead 280 and one group is associated with the implantable coil lead 282.

As noted above, cochlear implant 400 further includes a secondary module 455 that is configured to be positioned adjacent to an outer surface of the recipient's temporal bone 115, for example, adjacent to the superior portion 118. In this location at the skull exterior 127, the secondary module 455 is directly beneath the recipient's tissue and the secondary module is potentially subject to external stresses (e.g., impacts). As such, the secondary module 455 includes a housing 475 that is a robust element specifically designed to protect the internal components of the secondary module 455 from impacts or other external stresses. In certain examples, the housing 475 may be formed from titanium.

In general, the secondary module 455 includes electrical components that may be replaced and/or upgraded some period of time after initial implantation. In the specific embodiment of FIGS. 4A and 4B, the secondary module 455 includes a power supply 477. However, it is to be appreciated that the secondary module 455 may include other upgradeable electronics such as, for example, a microphone and/or a sound processor in a fully-implanted arrangement.

The use of the secondary module 455 results in the removal of certain components, such as the power supply, from the main implant module 450. The removal of components from the main implant module 450 assists in reducing the size of the main implant module.

As shown, the secondary module 455 is connected to the main implant module 450 via a lead 481. The lead 481 includes a first lead half 483(1), a second lead half 483(2), and an implantable connector 485. The first lead half 483(1) is connected to a feedthrough 479 that extends through housing 475 of the secondary module 455, while the second lead half 483(2) is connected to feedthrough 478(2) in main implant module 450.

The implantable connector 485 is a hermetically sealed releasable connector. As such, the secondary module 455 may be physically and electrically disconnected from the main implant module 450 and explanted without disturbing the location of the main implant module 450 or, more importantly, without disturbing the implanted location of the stimulating assembly 252 and/or the implantable coil 254 that are both connected to the main implant module 450.

As noted above, in the embodiment of FIGS. 4A and 4B, the main implant module 450 and the implantable coil 254 are positioned in different anatomical regions of the recipient's skull. In addition, the secondary module 455 is also positioned in an anatomical region that is separate from the anatomical regions of the main implant module 450 and the implantable coil 254 (i.e., the secondary module 455 is positioned at the skull exterior 127, the main implant module 450 is positioned in the mastoid cavity 125, and the implantable coil 254 is positioned within the middle ear cavity 106).

In operation, power and/or data is transferred from the outer coil 256 through the tympanic membrane 104 to implantable coil 254. As shown in FIG. 4B, electrical signals 229 corresponding to the power/data are sent from the implantable coil 254 along implantable coil lead 282 to transceiver unit 474 in main implant module 450. Power signals may then be sent to secondary module 455 (via lead 481) for use in charging the power supply 477. Data signals received via the implantable coil 254 may be used by the stimulator unit 472 to generate stimulation signals 231 that are provided to stimulating assembly 252 via stimulating assembly lead 282. The stimulation signals 231 are then delivered to the recipient via the stimulating contacts 248. The power supply 477 may be used to power various components of cochlear implant 400. As such, power signals 487 may also be sent to the main implant module 450 via lead assembly 481.

The above embodiments of FIGS. 2A-4B have been primarily described with reference to cochlear implants that include a sound processing unit disposed in a recipient's ear canal. It is to be appreciated that other embodiments may use a behind-the-ear sound processor (i.e., a sound processor worn on recipient's ear). In such embodiments, the outer coil is still located adjacent to the tympanic membrane, but is connected to other components via a cable extending from the behind-the-ear sound processor.

It is also to be appreciated that the use of an external sound processing unit is merely illustrative and that the techniques presented herein may also be used in arrangements having an implanted sound processor (e.g., mostly or totally implantable cochlear implants that require a means of recharging the battery, with is typically achieved via an RF link). Furthermore, it is to be appreciated that the individual components referenced herein, e.g., sound input element and the sound processor, may be distributed across more than one hearing prosthesis, e.g., two cochlear implants, and indeed across more than one type of device, e.g., a cochlear implant and a consumer electronic device or a remote control of the cochlear implant.

Figure 5A:
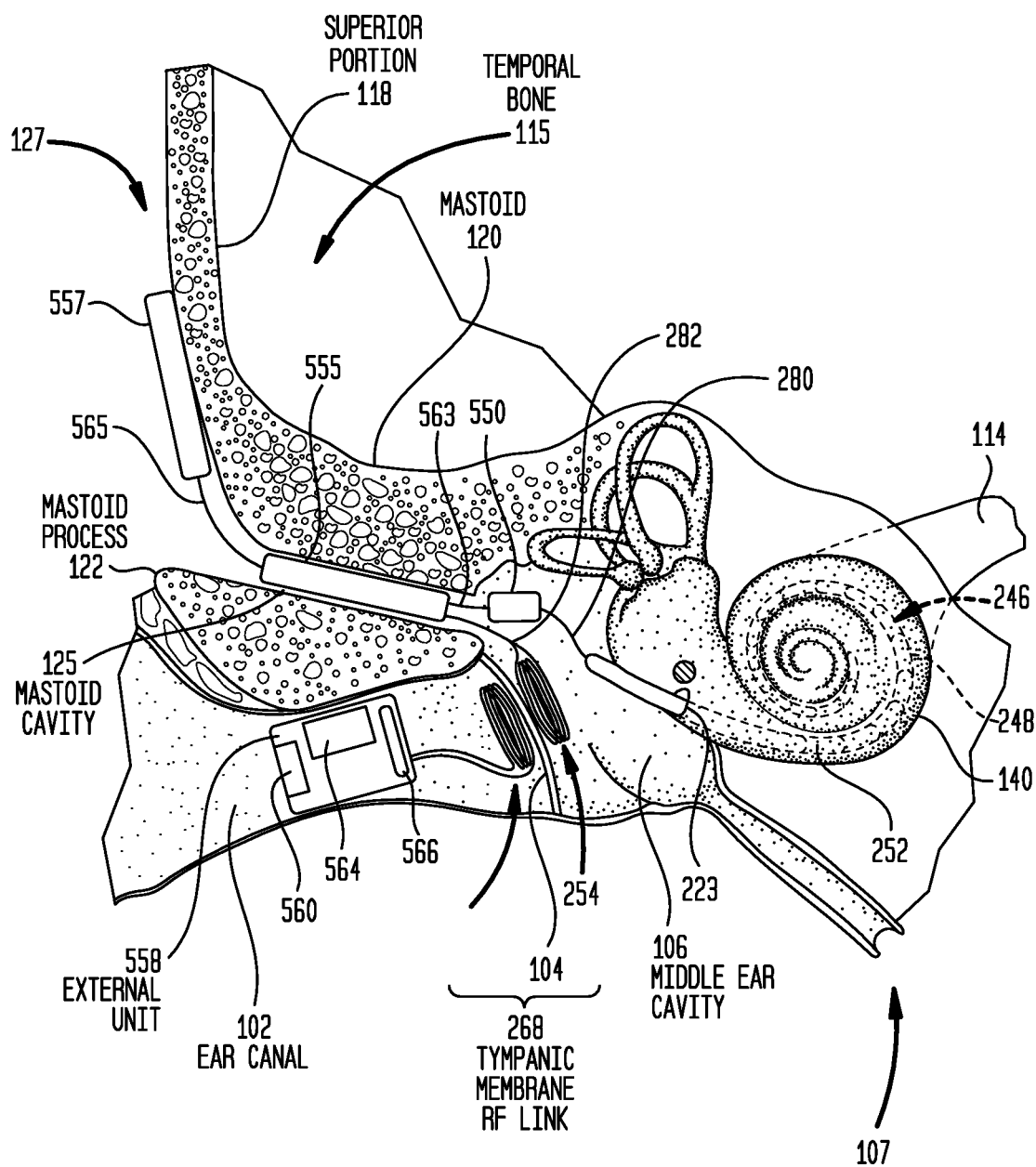
FIG. 5A is a schematic diagram illustrating a distributed implantable hearing system in accordance with embodiments presented herein implanted in a recipient.
Figure 5B:
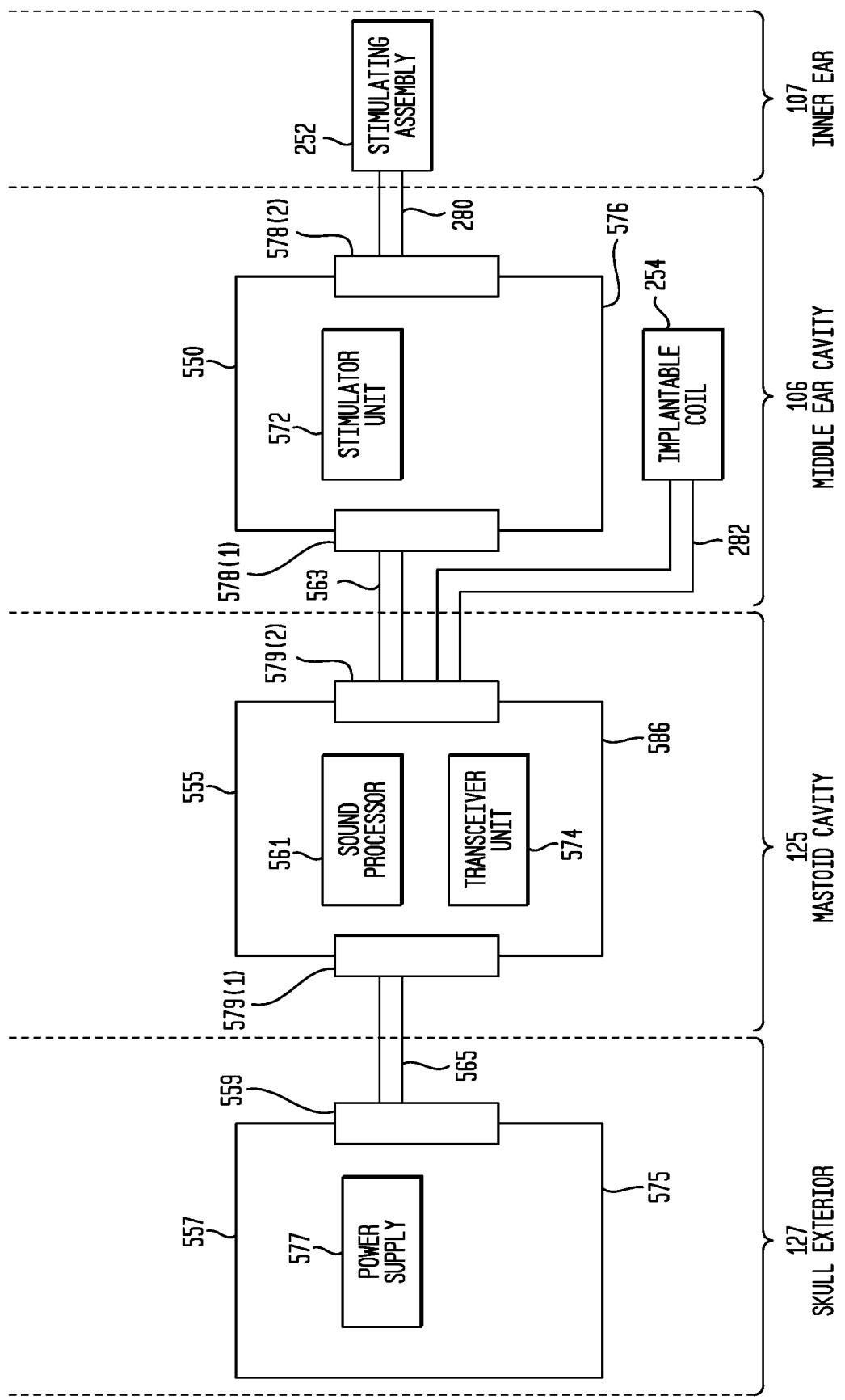
FIG. 5B is a block diagram of the implanted portions of the distributed implantable hearing system of FIG. 5A.

FIGS. 5A and 5B illustrate a distributed architecture for an exemplary mostly implantable cochlear implant 500 used in conjunction with a trans-tympanic membrane RF link. More specifically, FIG. 5A is a schematic diagram of the cochlear implant 500 shown implanted in the human anatomy illustrated in FIG. 1, while FIG. 5B is a block diagram of the implantable components of cochlear implant 500.

Cochlear implant 500 comprises a main implant module (implant body) 550, a first auxiliary module 555, a second auxiliary module 557, the elongate stimulating assembly 252, the implantable coil 254, the outer coil 256, and an external unit 558. The external unit 558 is an in-the-ear unit that is configured to be partially or fully positioned in a recipient's ear canal 102. The external unit 558 includes, or is connected to, one or more sound input elements 560 (e.g., microphones, telecoils, etc.) for detecting sound. The external unit 558 may also include a power supply (e.g., battery) 564 and a transceiver unit 566. The transceiver unit 566 is configured to provide power signals (from the power source 564) and electrical signals from the sound input element(s) 560 to the outer coil 256.

The outer coil 256 and the implantable coil 254 have substantially the same configuration as described above with reference to FIG. 2A so as to collectively form the trans-tympanic membrane RF link 268. Similarly, the elongate stimulating assembly 252 is, as described above, at least partially implanted in cochlea 140.

As shown in FIG. 5B, the main implant module 550 comprises a stimulator unit 572. The first auxiliary module 555 comprises a sound processor 561 and an internal receiver/transmitter unit 574, sometimes referred to herein as transceiver unit 574. The second auxiliary module 557 comprises a power supply 577.

The main implant module 550 comprises a hermetically sealed housing (case) 576 that includes feedthroughs 578(1) and 578(2) extending through the housing. As shown in FIG. 5A, the main implant module 550 is positioned within the recipient's middle ear cavity 106. That is, the main implant module 550 has a size and shape so as to be entirely positioned within the middle ear cavity 106. Because the main implant module 550 is recessed within middle ear cavity 106, the mastoid 120 effectively protects the main implant module 550 from external stresses (e.g., impacts). As such, similar to housing 376 of main implant module 350 in FIGS. 3A and 3B, the housing 576 need not be a robust element designed to protect the internal components. The housing 576 may have the same or substantially similar arrangement as the housing 376 of FIGS. 3A and 3B (e.g., ceramic feedthroughs with a thin titanium shell, a fully ceramic housing, a housing formed from a moldable ceramic, different shapes, etc.)

The first auxiliary module 555 comprises a hermetically sealed housing (case) 586 that includes feedthroughs 579(1) and 579(2) extending through the housing. As shown in FIG. 5A, the first auxiliary module 555 is fully recessed within the mastoid cavity 125. That is, the first auxiliary module 555 has a size and shape so as to be entirely positioned within the mastoid cavity 125. In this location, the first auxiliary module 555 is recessed within the recipient's mastoid 120. Because the first auxiliary module 555 is recessed within the mastoid 120, the mastoid effectively protects the first auxiliary module 555 from external stresses (e.g., impacts). As such, similar to housing 376 of main implant module 350 in FIGS. 3A and 3B, the housing 586 need not be a robust element designed to protect the internal components. The housing 586 may have the same or substantially similar arrangement as the housing 376 of FIGS. 3A and 3B (e.g., ceramic feedthroughs with a thin titanium shell, a fully ceramic housing, a housing formed from a moldable ceramic, different shapes, etc.)

The use of a non-robust housings 576 and 586 facilitates a reduction in the size of both the main implant module 550 and the first auxiliary module 555 relative to modules located at the skull exterior. However, similar to the embodiment of FIGS. 3A and 3B, further inventive aspects may also be utilized to create the main implant module 550 and the first auxiliary module 555. For example, a high level ASIC integration approach that minimizes the use of discrete components may be used for the design of either or both of the main implant module 550 and the first auxiliary module 555 (i.e., generation of an integrated electronics assembly for either or both of the main implant module 550 and the first auxiliary module 555). The integrated ASIC approach and/or other approaches described above effectively miniaturize the electrical components within main implant module 550 and the first auxiliary module 555.

Stimulating assembly 252 is connected to main implant module 550 via stimulating assembly lead 280 that is positioned in, and extends through, the middle ear cavity 106. The stimulating assembly lead 280 may include a plurality of electrically insulated conductors.

As noted, the implantable coil 254 is positioned in the middle ear cavity 106. As such, the implantable coil 254 is referred to herein as being distally positioned to the main implant module 550. That is, implantable coil 254 is physically separate from, and positioned at a distance from, the main implant module 550.

The implantable coil 254 is electrically connected to the first auxiliary module 555 via the implantable coil lead 282. In one embodiment, the implantable coil 254 is inserted through the mastoid cavity 125 and into middle ear cavity 106 where it is secured adjacent to the tympanic membrane 104. At the end of the surgical implantation, the implantable coil lead 282 is positioned in, and extends through, the middle ear cavity 106 and possibly a section the mastoid cavity 125, depending on the final position of the first auxiliary module 555. The implantable coil lead 282 may include a plurality of electrically insulated conductors.

As noted, the main implant module 550 includes a first feedthrough 578(1) and a second feedthrough 578(2). The stimulating assembly lead 280 is connected to the main implant module 550 via feedthrough 578(2). Additionally, the main implant module 550 is connected to the first auxiliary module 555 via a lead 563 that extends between feedthrough 578(1) and feedthrough 579(2). The implantable coil lead 282 electrically connects the implantable coil 254 to the first auxiliary module 555 via feedthrough 579(2).

As noted above, cochlear implant 500 further includes a second auxiliary module 557 that is configured to be positioned adjacent to an outer surface of the recipient's temporal bone 115, for example, adjacent to the superior portion 118. In this location at the skull exterior 127, the second auxiliary module 557 is directly beneath the recipient's tissue and the secondary module is potentially subject to external stresses (e.g., impacts). As such, the second auxiliary module 557 includes a housing 575 that is a robust element specifically designed to protect the internal components of the second auxiliary module 557 from impacts or other external stresses. In certain examples, the housing 575 may be formed from titanium.

In general, the second auxiliary module 557 includes electrical components that may be replaced and/or upgraded some period of time after initial implantation. In the specific embodiment of FIGS. 5A and 5B, the second auxiliary module 557 includes a power supply 577.

As shown, the second auxiliary module 557 is connected to the first auxiliary module 555 via a lead 565 (through a feedthrough 559 in the housing 575 and a feedthrough 579(1) in first auxiliary module 555).

The various modules 550, 555, and 557 are shown in FIGS. 5A and 5B shown by respective leads (cables). In certain embodiments, these leads may include releasable connectors that enable the modules 550, 555, and 557 to be physically and electrically disconnected from one another.

Figure 6:
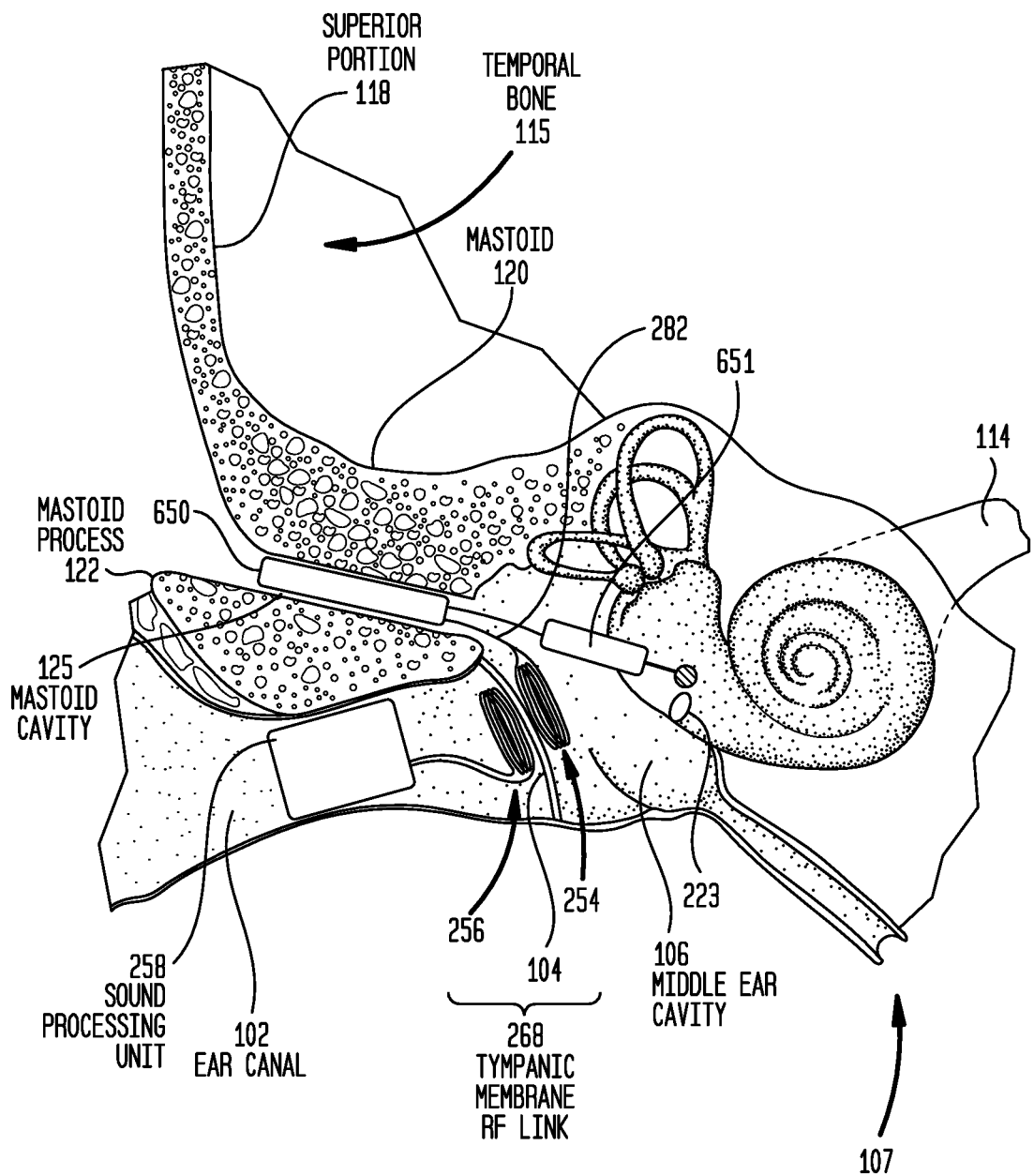
FIG. 6 is a schematic diagram illustrating another distributed implantable hearing system in accordance with embodiments presented herein implanted in a recipient.

Embodiments have been primarily described herein with reference to cochlear implants. It is to be appreciated that alternate embodiments may be directed to other implantable hearing prostheses, such as bone conduction devices or middle ear implants that stimulate the cochlea or ossicular chain using mechanical stimulation. For example, FIG. 6 is a schematic diagram of a direct acoustic stimulator 600 having a distributed architecture in accordance with embodiments presented herein that does not utilize a robust housing to protect components from external stresses. Direct acoustic stimulator 600 is shown implanted in the human anatomy illustrated in FIG. 1.

Direct acoustic stimulator 600 comprises a main implant module (implant body) 650, an implantable actuator 651, the implantable coil 254, the outer coil 256, and the sound processing unit 258. As described above with reference to FIG. 2A, the sound processing unit 258 is an in-the-ear unit that is configured to be partially or fully positioned in a recipient's ear canal 102. For ease of illustration, the components of sound processing unit 258 have been omitted from FIG. 3A.

The outer coil 256 and the implantable coil 254 have substantially the same configuration as described above with reference to FIG. 2A so as to collectively form the transtympanic membrane RF link 268. The actuator 651 is mechanically coupled to the recipient's inner ear 107. Alternately it may be coupled to the inner ear via the ossicles (not shown).

The main implant module 650 may have a similar arrangement to the arrangement of FIGS. 3A and 3B (i.e., comprising a rechargeable power supply, a stimulator unit, and a transceiver unit). However, in the embodiment of FIG. 6 the stimulator unit within main implant module 650 comprises components that are configured to drive the actuator 651 so as to generate vibration of the fluid within the recipient's cochlea 140.

Again, similar to the arrangement of FIGS. 3A and 3B, the main implant module 650 comprises a hermetically sealed housing configured to be fully recessed within the mastoid cavity 125. That is, the main implant module 650 has a size and shape so as to be entirely positioned within the mastoid cavity 125. Because the main implant module 650 is recessed within the mastoid 120, the mastoid effectively protects the main implant module 650 from external stresses (e.g., impacts). As such, the housing of main implant module 650 need not be a robust element designed to protect the internal components and may have the same or substantially similar arrangement as the housing 376 of FIGS. 3A and 3B (e.g., ceramic feedthroughs with a thin titanium shell, a fully ceramic housing, a housing formed from a moldable ceramic, different shapes, etc.)

The use of a non-robust housing of main implant module 650 facilitates a reduction in the size of both the main implant module relative to modules located at the skull exterior. However, similar to the embodiment of FIGS. 3A and 3B, further inventive aspects may also be utilized to create the main implant module 650. For example, a high level ASIC integration approach that minimizes the use of discrete components may be used for the design of the main implant module 650 (i.e., generation of an integrated electronics assembly for the main implant module 650). The integrated ASIC approach and/or other approaches described above effectively miniaturize the electrical components within main implant module 650.

Figure 7:
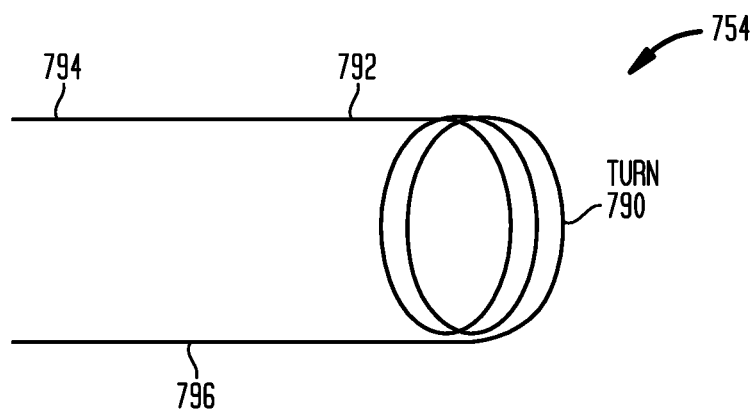
FIG. 7 is a perspective view of an implantable coil configured to be used as part of a trans-tympanic membrane radio-frequency link in accordance with embodiments presented herein.

FIG. 7 is a schematic diagram illustrating one arrangement for an implantable coil 754 that may be part of a trans-tympanic membrane RF link in accordance with embodiments presented herein. The implantable coil 754 comprises a single-strand or multi-strand wire (e.g., platinum or gold) 792 formed into one or more wire turns 790. In the embodiment of FIG. 7, the wire turns 790 are substantially parallel to one another and have a generally circular shape. That is, the implantable coil 754 has a general helical shape.

The implantable coil 754 has a first end 794 and a second end 796. When the implantable coil 754 is energized (though inductive coupling with an outer coil), current will flow through the implantable coil 754. While the current is alternating current (AC), at an instant current is flowing in one direction in the external coil and current will also flow in one direction in the implanted coil.

As noted above, for ease of illustration the recipient's ossicular chain 132 (i.e., malleus 108, the incus 109 and the stapes 111) has been omitted from FIGS. 2A-4B. It is to be appreciated that the removal of the recipient's ossicular chain 132 may not be necessary and, in fact, undesirable in certain circumstances. For example, certain cochlear implant recipients may have some residual hearing capabilities that can be used with a cochlear implant (i.e., utilize the cochlear implant for high frequency hearing and utilize the residual hearing for low frequency hearing). To retain the residual hearing capabilities, it is important not to damage or interfere with the operation of the ossicular chain 132 during implantation of the cochlear implant. To implant an implantable coil having substantially circular turns, such as implantable coil 754 of FIG. 7, the surgeon is required to break the ossicular chain during implantation of the implantable coil. More specifically, since the implantable coil is located directly adjacent to the tympanic membrane to which the malleus 108 is attached, the surgeon must either break the malleus, or separate the malleus from the tympanic membrane, so that the implantable coil can be properly located.

Figure 8:
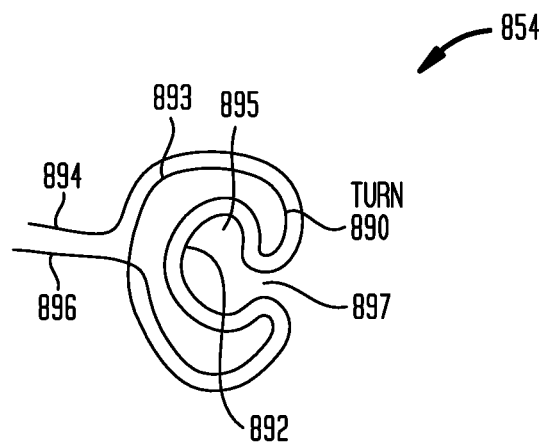
FIG. 8 is a perspective view of another implantable coil configured to be used as part of a trans-tympanic membrane radio-frequency link in accordance with embodiments presented herein.

FIG. 8 is a schematic diagram illustrating an arrangement for an implantable coil 854 that may be implanted without damaging or interfering with the operation of the ossicular chain 132. The implantable coil 854 comprises a single-strand or multi-strand wire (e.g., platinum or gold) 892 formed into a one or more wire turns 890. In the embodiment of FIG. 8, the wire turns 890 are substantially parallel to one another and have a generally fabiform shape (i.e., fabiform-shaped wire turns 890). That is, the wire turns 890 each have a general kidney-bean shape. The fabiform shape of wire turns 890 may be alternatively defined as having two substantially concentric and conjoined semicircular portions that are joined at the open ends and wherein one of the semicircular portions is smaller that the other semicircular portion.

For example, FIG. 8 illustrates a wire turn 890 having an outer semicircular portion 893 and an inner semicircular portion 891. The outer semicircular portion 893 and the inner semicircular portion 891 are substantially concentric and the open ends of the inner semicircular portion 891 are connected to, and contiguous with, the open ends of the outer semicircular portion 893. The inner semicircular portion 891 is smaller than the outer semicircular portion 893.

When implanted within a recipient, the implantable coil 854 is configured to be positioned around the recipient's malleus 108. More specifically, the inner semicircular portions 891 of the wire turns 890 define a generally oval aperture 895 that is contiguous with a slot 897. During implantation, the malleus 108 may pass through the slot 897 so as to have a final position within the aperture 895.

The implantable coil 854 has a first end 894 and a second end 896. When the implantable coil 854 is energized (though inductive coupling with an outer coil), current will flow through the implantable coil 854 While the current is AC, at an instant when current is flowing in one direction in the external coil and current will also flow in one direction in the implanted coil. For example, when energized, current may flow in the direction of first end 894 (i.e., from the direction of second end 896) only or current may flow in the direction of second end 896 only (i.e., from the direction of first end 894). The single direction of current flow (at any instant) may depend on the orientations of the implantable coil 854 and the corresponding outer coil and/or the direction of current flow in the outer coil. In certain embodiments, the outer coil of a trans-tympanic RF link will have the configuration shown in FIG. 7. In this case, there may be current induced at 895 which tends to oppose the current induced at 893. However the coil area at 893 is larger than at 895 so the current induced at 893 will dominate and will dictate the direction of current flow.

Embodiments presented herein are generally directed to a miniaturized implantable hearing prosthesis that uses a simple and small RF coil implanted into the middle ear space adjacent to the tympanic membrane and a module implanted in the mastoid cavity. No magnets are utilized for the trans-tympanic RF link and the implant has improved MIII compatibility over standard configurations. Additionally, the module implanted in the mastoid cavity is protected from external stresses by the recipient's bone, thus the module need not be as robust as a module positioned at the outer surface of a recipient's skull.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:
1. A method, comprising:
   surgically forming a mastoid cavity through a mastoid bone of a recipient of a hearing prosthesis, wherein the mastoid cavity has a proximal end at an outer surface of the mastoid bone and a distal end at a middle ear cavity of the recipient;
   implanting a main implant module of the hearing prosthesis fully within the surgically formed mastoid cavity, wherein the main implant module includes a stimulator unit and a transceiver unit; and
   implanting an implantable coil in the middle ear cavity, wherein the implantable coil is electrically connected to the main implant module via one or more wires extending through the distal end of the mastoid cavity.

2. The method of claim 1, comprising:
positioning an outer coil in an ear of the recipient proximate to the implantable coil so as to form a radio-frequency link with the implantable coil.

3. The method of claim 2, wherein positioning the outer coil in the ear of the recipient comprises:
positioning the outer coil in an ear canal of the recipient at an outer surface of a tympanic membrane in the ear.

4. The method of claim 3, wherein the outer coil comprises a plurality of turns of wire each having an outer diameter that is larger than an inner dimension of the ear canal, and wherein positioning the outer coil in the ear canal of the recipient comprises:
positioning the outer coil such that the ear canal compresses the plurality of turns of wire.

5. The method of claim 2, further comprising:
positioning a sound processing unit in the ear of the recipient, wherein the sound processing unit is electrically connected to the outer coil, and wherein the sound processing unit includes one or more sound input elements configured to receive sound signals and a sound processor configured to convert the sound signals into coded data signals for transmission to the main implant module via the radio-frequency link.

6. The method of claim 1, further comprising:
prior to implanting the main implant module, implanting an elongate stimulating assembly comprising a plurality of stimulating contacts into a cochlea of the recipient via the surgically formed mastoid cavity.

7. The method of claim 6, wherein the main implant module includes an elongate axis, and wherein implanting the main implant module comprises:
implanting the main implant module in the surgically formed mastoid cavity in an orientation in which the elongate axis of the main implant module is substantially in-line with a proximal end of the elongate stimulating assembly.

8. The method of claim 1, wherein implanting the implantable coil comprises:
prior to implanting the main implant module, inserting the implantable coil through the surgically formed mastoid cavity and into the middle ear cavity.

9. The method of claim 1, wherein the main implant module includes a hermetically-sealed housing formed from a moldable ceramic material.

10. The method of claim 1, wherein the main implant module includes a hermetically-sealed housing and a feedthrough each formed from a ceramic material.

11. The method of claim 1, wherein the main implant module includes a rechargeable power source.

12. A hearing system, comprising:
an implant module configured to be fully recessed within a mastoid cavity surgically formed within a mastoid bone of a recipient, wherein the mastoid cavity is surgically formed and comprises a proximal end at an outer surface of the mastoid bone and a distal end at a middle ear cavity of the recipient, and wherein the implant module includes a stimulator unit and a transceiver unit;
an implantable coil configured to be implanted in the middle ear cavity, wherein the implantable coil is electrically connected to the implant module via one or more wires extending through a distal end of the mastoid cavity; and
an outer coil positioned in an ear canal of the recipient proximate to an ear drum of the recipient the implantable coil so as to form a radio-frequency link with the implantable coil.

13. The hearing system of claim 12, further comprising:
an elongate stimulating assembly configured to be implanted in a cochlea of the recipient via the mastoid cavity, wherein the elongate stimulating assembly comprises a plurality of stimulating contacts.

14. The hearing system of claim 13, wherein the implant module includes an elongate axis, and wherein the implant module is configured to be implanted in the mastoid cavity in an orientation in which the elongate axis of the implant module is substantially in-line with a proximal end of the elongate stimulating assembly.

15. The hearing system of claim 12, wherein the outer coil is configured to be positioned in an ear canal of the recipient at an outer surface of a tympanic membrane in the ear.

16. The hearing system of claim 15, wherein the outer coil comprises a plurality of turns of wire each having an outer diameter that is larger than an inner dimension of the ear canal, and wherein the outer coil is configured to be positioned in the ear canal of the recipient such that the ear canal compresses the plurality of turns of wire.

17. The hearing system of claim 12, wherein the implant module includes a hermetically-sealed housing formed from a moldable ceramic material.

18. The hearing system of claim 12, wherein the implant module includes a hermetically-sealed housing and a feedthrough each formed from a ceramic material.

19. The hearing system of claim 12, further comprising:
a sound processing unit configured to be positioned in the ear of the recipient, wherein the sound processing unit is electrically connected to the outer coil, and wherein the sound processing unit includes one or more sound input elements configured to receive sound signals and a sound processor configured to convert the sound signals into coded data signals for transmission to the implant module via the radio-frequency link.

20. The hearing system of claim 12, wherein the implant module includes a rechargeable power source.

21. The hearing system of claim 12, wherein the implant module comprises a first implant module, and wherein the hearing system further comprises one or more auxiliary implant modules configured to be implanted in the mastoid cavity or abutting an outer surface of the recipient's skull.

22. The hearing system of claim 12, wherein the hearing system is a cochlear implant.

23. The hearing system of claim 12, wherein the hearing system is a direct acoustic stimulator.

* * * * *